(12) United States Patent  
Freishtat

(10) Patent No.: US 7,919,265 B2  
(45) Date of Patent: Apr. 5, 2011

(54) ANTIBODY-BASED METHOD FOR ISOLATING TH1 AND TH2 HELPER LYMPHOCYTES FROM HUMAN PERIPHERAL BLOOD

(75) Inventor: Robert J. Freishtat, Potomac, MD (US)

(73) Assignee: Children's Research Institute, Washington, DC (US)

(*) Notice: Subject to any disclaimer, the term of this patent is extended or adjusted under 35 U.S.C. 154(b) by 869 days.

(21) Appl. No.: 11/471,417

(22) Filed: Jun. 21, 2006

(65) Prior Publication Data

US 2007/0298441 A1    Dec. 27, 2007

(51) Int. Cl.
*G01N 33/00* (2006.01)
(52) U.S. Cl. ........ 435/7.24; 435/7.2; 435/7.25; 435/7.5; 435/325; 435/372.3; 436/523; 436/526; 436/538; 436/64; 436/177
(58) Field of Classification Search ........... 435/7.2, 435/7.24, 7.25, 7.5, 7.92, 7.94, 40.5, 372, 435/372.3, 287.2, 325; 436/523, 526, 538, 436/63, 64, 161, 175, 177
See application file for complete search history.

(56) References Cited

U.S. PATENT DOCUMENTS

| | | | |
|---|---|---|---|
| 6,488,930 B1 * | 12/2002 | Wu et al. | 424/143.1 |
| 6,913,924 B2 * | 7/2005 | Blom et al. | 435/325 |
| 2002/0081635 A1 * | 6/2002 | Thomas et al. | 435/7.21 |
| 2006/0239962 A1 * | 10/2006 | Banchereau | 424/85.1 |

OTHER PUBLICATIONS

Freishtat et al. NKG2A and CD56 Are Coexpressed on Activated Th2 but not Th1 Lymphocytes, Human Immunology 66: 1223-1234 (2005).*
Robert J. Freishtat, M.D., MPH, et al. "NKG2A and CD56 Are Coexpressed on Activated TH2 but Not TH1 Lymphocytes", Human Immunology 66, 1223-1234 (2005).

* cited by examiner

*Primary Examiner* — Gailene R Gabel
(74) *Attorney, Agent, or Firm* — Blank Rome LLP

(57) ABSTRACT

A negative isolation method for separately isolating preparations of Th1 and Th2 helper lymphocytes from peripheral blood mononuclear cells involving the use of novel combinations of monoclonal antibodies to separately sequester specific Th1 and Th2 lymphocytes and contaminating leukocytes and erythrocytes, adding a magnetic colloid to the cells, and using a magnetic column for fractionation of Th1 and Th2 cells. Imbalances in the relative numbers of Th1 and Th2 lymphocytes can be used in the diagnosis and prognosis of human diseases.

3 Claims, 1 Drawing Sheet

Figure 1:
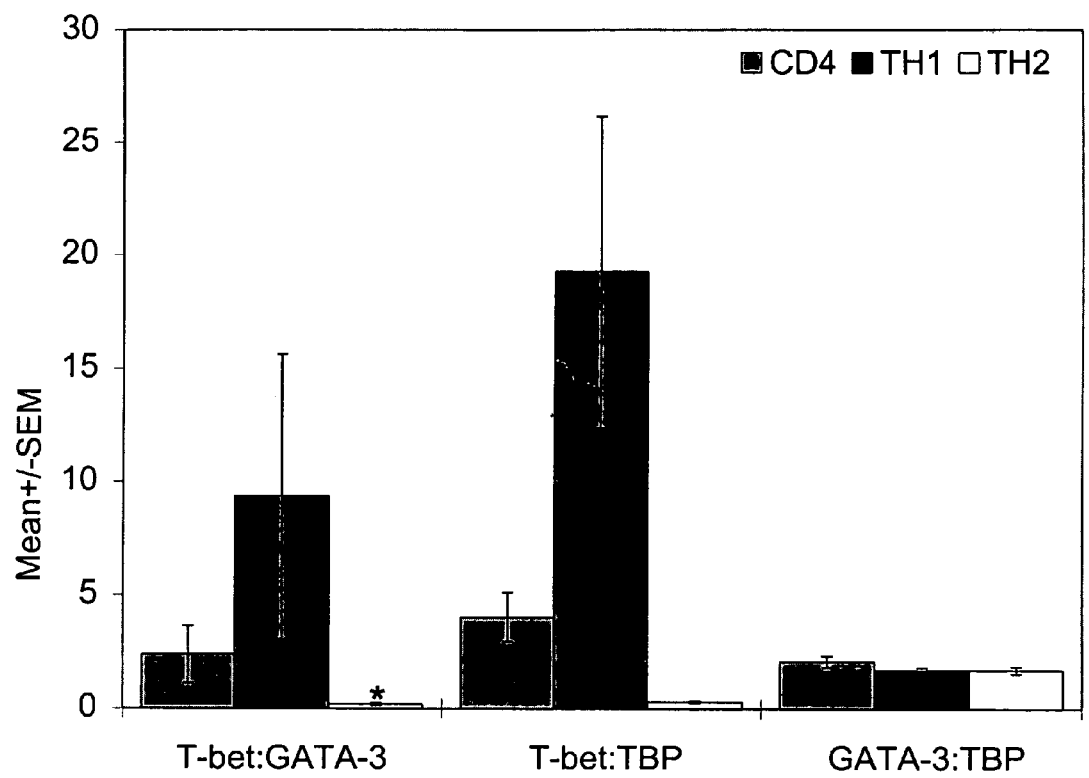

ANTIBODY-BASED METHOD FOR ISOLATING TH1 AND TH2 HELPER LYMPHOCYTES FROM HUMAN PERIPHERAL BLOOD

FIELD OF THE INVENTION

The invention relates to the isolation of T-helper lymphocytes from human peripheral blood. More specifically, the invention is a method of negative isolation of Th1 and Th2 lymphocytes using monoclonal antibodies.

BACKGROUND OF THE INVENTION

In response to infection, numerous cell types within the vertebrate immune system act in concert to effect the rapid and efficient clearance of the invading pathogen. Among these cell types are T cells, which develop in the thymus and which are responsible for cell-mediated immunity. T cells are divided into several major subclasses, including cytotoxic T cells, which kill virus-infected cells, as well as two classes of regulatory cells, called helper T cells (Th cells) and suppressor T cells, which act to modulate the activity of other immune cells. During chronic infections, Th cells develop into at least two phenotypically and functionally distinct effector populations, Th1 and Th2 lymphocytes. Th1 cells produce IFN-.gamma and IL-2, which are commonly associated with cell-mediated immune responses against various intracellular pathogens, whereas Th2 cells produce cytokines such as IL-4, IL-5, IL-6, IL-10 and IL-13, that are crucial to control extracellular helminthic infections.

In certain cases, the number, activity, or other properties of Th1 or Th2 cells can become abnormal, and these cell types can play a role in one or another disease or condition. For example, Th1 cells have been associated with organ-specific autoimmune diseases, delayed-type hypersensitivity, and transplant rejection. In addition, imbalance of Th2 cytokines are observed in various atopic and allergic diseases, which are usually accompanied by increased production of IgG1 and IgE as well as the activation of eosinophils and mast cells.

Cytokines such as IL-12 and IL-4 have dominant roles in determining the outcome of Th differentiation into Th1 and Th2 subsets, respectively. These cytokines bind to their cognate receptors, leading to activation of the Janus family of kinases and the latent transcription factors known as signal transducers and activators of transcription (STATs). For example, in Th1 cells, following the binding of IL-12 to its cognate receptor, STAT4 is activated, thereby leading to the production of IFN-.gamma. Accordingly, STAT4-deficient mice are defective in Th1 differentiation and do not respond to intracellular pathogens such as Listeria monocytogenes. In Th2 cells, IL-4 leads to the activation of STAT6, which is essential for the development of these cells. Accordingly, STAT6-deficient mice have an impaired ability to produce IL-4-secreting Th2 cells, thereby resulting in a failure to expel intestinal helminths. Interestingly, these STAT6 mutant mice are protected from antigen-induced airway hyperresponsiveness.

Additional reports have identified various genes that are differentially expressed in Th1 and Th2 cells. For example, the transcription factor ERM is selectively expressed in Th1 cells, and, in Th2 cells, GATA-3 and c-Maf are selectively expressed. GATA-3 is required for the expression of certain Th2 specific genes, can lead to the expression of IL-4 and IL-5 in Th1 cells, and inhibits the production of IFN-γ in Th1 cells. See, e.g., Zheng et al. Cell 89(4):587 (1997); Zhang et al., J. Biol. Chem. 272:21597 (1997); or Ferber et al., Clin. Immunol. 91:134 (1999). Additionally, several cell surface proteins are also differentially expressed in the Th1 and Th2 subsets. For example, Th1 cells express various chemokine receptors such as CXCR3, CCR1, and CCR5. Th2 cells, in contrast, express CD30 as well as various chemokine receptors such as CCR8.

Various cell surface proteins have been identified as having four-transmembrane domains, and are called tetraspanins, or transmembrane 4 superfamily (TM4SF). Such proteins, including, for example, CD4, CD81, CD9, and CD20, have a strong propensity to form molecular associations with other cell surface molecules. CD81, for example, which is expressed in both T and B lymphocytes, is found in a multimolecular complex with CD19 and the complement receptors 1 and 2 in B lymphocytes. Previous studies have demonstrated that this complex collectively regulates the threshold for antigen receptor-mediated B cell activation. In T cells, CD81 contributes to cell proliferation as well as to IL-2 and IL-4 production. Other four transmembrane proteins have been associated with various cellular activities, including receptor activity, cell-cell binding, integrin binding and/or signaling, or channel activity, e.g., $Ca^{2+}$ channel activity (see, e.g., Bubien et al., J Cell Bio 121(5):1121 (1993)).

Glycophorin A (CD235a) is a 131-amino acid asialoglycoprotein that spans the membrane of the erythrocyte once. CD235a has an extracellular peptide portion that is antigenic.

The National Institutes of Health (USA) has conducted a Phase II/III study evaluating the effect of IL-2 on preservation of the CD4 Th-lymphocytes after interruption of anti-retroviral treatment (AVT) of infected patients with CD4 Th-lymphocyte counts greater than 500 cells/mm3 who had received AVT (NCTOO071890 Identifier). Th1s study examined whether interleukin-2 (IL-2) given before the interruption of anti-retroviral (ART) treatment could significantly extend the period of time that a patient is temporarily not taking ART treatment and also preserve CD4 counts above 350 cells per microliter. There was an evaluation of the toxicity, or extremely harmful effects, of ART, and the effect on quality of life. The use of ART medications has greatly improved the condition and mortality of HIV-infected patients. But when used long term, those medications have been associated with great toxicities and medication fatigue. As a result, patients may not adhere to ART use, and resistance to viruses may grow. The CD4 molecule is on the surface of Th-lymphocytes, or It serves as the primary receptor for HIV-1 and HIV-2, allowing the virus to gain entry into its host. The CD4 count increases immediately in response to ART, giving an estimate of the state of a patient's immune system. Thus, it is a strong marker of the immediate risk of an opportunistic infection, one that takes advantage of a person's weakened immune system. IL-2 is a molecule naturally produced by activated T cells. In patients with HIV, IL-2 treatment can increase CD4 counts but the clinical importance of this increase was not clear. This study compared the decline in Th CD4 count, when ARV was interrupted. This type of clinical study would be greatly aided were there a simple means of isolating Th lymphocytes from patient blood quickly and easily.

Rapid access to "clean" Th1 and Th2 lymphocytes would also be an asset in: studies of the reduction of Th1 lymphocytes in peripheral blood in: Grave's Disease and Type 1 Diabetes (Matsuura, A Y et al., Endocrin. J. May 23, 2006); immunotherapeutics (Wang, C Y et al., Vaccine; 23:49 (2005)); tracking the severity of human asthma or assessing the effectiveness of immunomodulating drugs used to treat asthma and other autoimmune diseases; and, other Th1/Th2- balance related diseases, e.g., where allergy skin testing by RAST is not possible; and, other antigen-related diseases.

These goals have been achieved by the development of a novel and useful method of isolating, separately, Th1 and Th2 lymphocytes from human peripheral blood. This method is described below.

SUMMARY OF THE INVENTION

The invention comprises a negative isolation method for separately isolating Th1 and Th2 lymphocytes from a mixture of human peripheral blood mononuclear cells wherein mixtures of specific monoclonal antibodies are used to remove all but the desired T-helper lymphocytes, as well as contaminating erythrocytes.

In one embodiment, Th1 cells are isolated by sequestering Th2 cells in the lymphocyte mixture with anti-CRTh2-biotin and antiCCR4-biotin monoclonal antibodies, and sequestering the remaining undesired lymphocytes with monoclonal antibodies directed against CD8, CD16, CD19, and CD56 lymphocyte cell surface antigens, and directed against glycophorin A to sequester erythrocytes, then adsorbing the antibody complexes onto a magnetic colloid, and separating the Th1 cells on a magnetic column.

In another embodiment, Th2 cells are isolated similarly, except that Th1 cells are sequestered by anti-CD29 (beta 1 integrin)-biotin and anti-CXCR3 monoclonal antibody, and the remaining undesired lymphocytes are sequestered with monoclonal antibodies directed against CD8, CD14, CD16, CD19, CD56, and glycophorin A.

In additional embodiments, imbalances in the relative numbers of Th1 and Th2 lymphocytes in the enriched isolates are used in the diagnosis and prognosis in various diseases involving the human immune system.

FIGURE

FIG. 1 compares T-bet:GATA-3, T-bet:TAPA binding proteins (TBP), and GATA-3:TBP mRNA rations, in Th1 and Th2. Lymphocyte subsets and nonfractionated CD4+ T lymphocytes, by quantitative RT-PCR. *p=0.04

DETAILED DESCRIPTION OF THE PREFERRED EMBODIMENTS

We have developed a negative isolation procedure by which monoclonal antibodies are used separately to isolate Th1 and Th2 lymphocytes from peripheral blood mononuclear cells isolated using a Ficoll Paque PLUS (Amersham Biosci., Piscataway, N.J.). The antibodies used to isolate Th2 cells were obtained from Miltenyi Biotec (Cologne, Del.), Auburn, Calif. (USA), and those to isolate Th1 cells from Research Diagnostics, Inc., Flanders, N.J. (USA). The monoclonal antibody combinations used for the negative isolations were chosen based on differential prevalence of surface markers on each cell type, as reported by others (see, Freishtat, R J et al., *Hum Immunol* 66(12):1223 (2005) refs. 33-46). Cocktails of these anti-surface marker monoclonal antibodies that isolate all but CD4+ cells were obtained from Stem Cell Technologies, Vancouver, BC, Canada. Using these combinations of monoclonal antibodies, we developed a method for the negative isolation of Th1 and Th2 cells. Such methods, that are described in detail in the Examples below, yielded an over 90% enrichment for Th1 cells and over 84% for Th2 cells.

Validation of this negative isolation protocol can be carried out by flow cytometry and RT-PCR analyses, as described in the Examples below.

The Th1 and Th2 lymphocytes, separately isolated by the inventive methods, can be quantified by standard methods of cell counting, the ratios of Th1 to Th2 lymphocytes calculated, and these ratios used in human disease diagnostic and prognostic methods. For example, a reduced ratio, that is, a lowering of Th1 T lymphocytes relative to Th2 cells, is more associated with patients having both type 1 diabetes and Grave's disease, both autoimmune diseases, than in those with diabetes alone (Aso, Y. et al. Endocrin. J. Mar. 23, 2006 e-publication). For another example, an increase in the Th1:Th2 ratio is associated with Crohn's disease, and perhaps also Crohn-like Inflammatory Bowel Syndrome (e-report, May 1, 2006, National Institutes of Health). For yet another example, an imbalance between Th1 and Th2 lymphocytes is diagnostic for the pathogenesis of syncytial virus bronchiolitis and as to the severity of the infection (Pinto, R A, *Pediatrics*, 117:878 (2006)). Thus, the balance between numbers of Th1 and Th2 lymphocytes as determined by the present invention is prognostic or diagnostic of a variuety of human diseases.

The following specific examples are not intended to limit the claims in any way, claims being limited only by the disclosure in the specification.

EXAMPLE 1

Isolation of Peripheral Blood Mononuclear Cells

Cell separation procedures were initiated within 30 mins. of blood collection from 11 apparently healthy, non-atopic, non-asthmatic volunteers between the ages of 18 and 30.

Whole blood was placed in conical tubes and centrifuged at low speed. Platelet-rich plasma was removed, and the remaining blood cell concentrate was diluted to 30 ml with 2% fetal bovine serum (FBS) in 1% PBS, and then centrifuged over Ficoll Paque PLUS density medium to isolate the peripheral blood mononuclear (PMBC) layer. The cells were washed and resuspended in PBS-2% FBS.

EXAMPLE 2

Isolation of Th1 Lymphocytes

The PBMC cells were counted in a hemocytometer to ensure a cell concentration of $<8 \times 10^7$. Nondifferentiated Th cells, Th1 cells or Th2 cells were negatively isolated using the StemSep procedure (see p. 10, StemCell Technologies, Vancouver, BC, Canada, Technical Manual), except for the addition of inventive novel combinations of monoclonal antibodies developed and validated by us.

For the negative isolation of Th1 cells, approximately $5 \times 10^6$ cells were treated at 4° C. with monoclonal anti-CRTh2-Biotin and anti-CCR4-biotin antibodies (Miltenyi Biotec) to bind the Th2 cells. After one wash, cells were incubated at room temperature for 15 mins. with anti-biotin tetramers (StemCell) plus a cocktail containing monoclonal antibodies to lymphocyte CD8, CD16, CD19, and CD56, and to erythrocyte glycophorin A. Samples were centrifuged, the supernatant fluids removed, and the cell pellet containing antibody-bound PBMCs and unbound Th1 were suspended in PBS-2% FBS. Following a final incubation for 15 mins. at room temperature with StemCell magnetic colloid, samples were run through a magnetic column. Eluted Th1 cells were isolated by centrifugation at low speed for further uses.

EXAMPLE 3

Isolation of Th2 Lymphocytes

The negative isolation of Th2 was similar, except that samples were first treated with anti-CD29 (beta 1 integrin)-biotin monoclonal antibodies (Research Diagnostics) and anti-CxCR3-biotin to bind Th1 cells at 4° C. for 10 mins. Samples were washed and then incubated for 15 mins. at room temperature with a monoclonal antibody cocktail containing anti-CD8, anti-CD14, anti-CD16, anti-CD19, anti-CD56, and anti-glycophorinA. The remaining isolation procedures were the same as for Th1.

EXAMPLE 4

Purity of Th1 and Th2 isolates

Validation of the negative isolation monoclonal antibody cocktails was confirmed both by flow cytometry (FACSCalibur System, BD) as described by Freishstat et al. (2005) above, and by RT-PCR also as described in Freishtat et al. Flow cytometry showed that Th1 and Th2 samples were depleted of cells positive for markers contained in the isolation cocktails.

Th1 and Th2 enrichment was also characterized using RT-PCR as described in Chakir et al. *J. Immunol Meth.* 278:157 (2003). This method uses the T-bet:GATA-3 mRNA ratio to estimate the Th1:Th2 ratio within each isolate. As seen in FIG. 1, the mean T-bet:GATA-3 rations showed purities of 90.3% for Th1 and 84.1% for the enriched Th2 cells. The mean T-bet:GATA-3 ratio for the Th 2 cells was statistically significantly different from that of a group of nonfractionated CD4+ Th-enriched control cells. The Th1 cells were not statistically different from the nonfractionated Th or Th2 cells.

I claim:

1. A method for isolating Th2 lymphocytes from a mixture of human peripheral blood mononuclear cells (PBMCs), comprising the steps of:
    (i) contacting said mixture with anti-Th1 monoclonal antibodies comprising anti-CD29-biotin and anti-CXCR3-biotin clones,
    (ii) contacting said mixture with antibodies that bind to cell surface antigens of non-Th2 leucocytes, wherein the cell surface antigens of the non-Th2 leucocytes comprises CD8, CD14, CD16, CD19, and CD56;
    (iii) contacting said mixture with an antibody to an erythrocyte cell surface antigen;
    (iv) contacting the mixture in step in with a magnetic colloid that binds to the antibodies in steps (i) to (iii) to magnetically label the Th1 lymphocytes, non-Th2 leukocytes, and erythrocytes; and
    (v) separating the magnetically labeled cells from the Th2 lymphocytes with a magnet to obtain isolated Th2 lymphocytes.

2. The method of claim 1, wherein said antibody directed to said erythrocyte antigen is an anti-glycophorin A (CD235a) antibody.

3. The method of claim 1, wherein said Th2 lymphocytes collected from step (v) are at least 84% pure.

* * * * *